United States Patent [19]
Vaiani et al.

[11] Patent Number: 5,374,285
[45] Date of Patent: Dec. 20, 1994

[54] SPINAL ELECTRODE CATHETER

[75] Inventors: Paolo Vaiani, Scarperia; Claudio Gibelli, Arese; Enzo Borghi, Bologna, all of Italy

[73] Assignee: Aries S.R.L., Florence, Italy

[21] Appl. No.: 100,049

[22] Filed: Jul. 30, 1993

[30] Foreign Application Priority Data

Jul. 31, 1992 [EP] European Pat. Off. ........ 92830434.4

[51] Int. Cl.⁵ .............................................. A61N 1/05
[52] U.S. Cl. ................... 607/117; 607/116; 29/857; 29/850
[58] Field of Search ............. 607/117, 116, 115, 120, 607/122; 128/642; 29/857, 850, 861

[56] References Cited

U.S. PATENT DOCUMENTS

| | | |
|---|---|---|
| 3,769,984 | 11/1973 | Muench . |
| 4,379,462 | 4/1983 | Borkan et al. . |
| 4,590,950 | 5/1986 | Iwaszkiewicz et al. . |
| 4,800,898 | 1/1989 | Hess et al. . |
| 4,850,359 | 7/1989 | Putz .................................. 607/116 |
| 5,119,832 | 6/1992 | Xavier . |

*Primary Examiner*—William E. Kamm
*Assistant Examiner*—Kennedy J. Schaetzle
*Attorney, Agent, or Firm*—Fay, Sharpe, Beall, Fagan, Minnich & McKee

[57] ABSTRACT

The electrode catheter comprises a flexible spiral wound element accommodated coaxially within and extending the entire length of a first sheath such a way as to provide a core ensuring rigidity, for the purposes of the initial implantation, and flexibility to allow subsequent adaptation of the catheter to the subcutaneous cavity ultimately occupied. The spiral wound element carries a set of wires, each bared at the distal end, which break out of respective holes in the sheath to connect with relative terminals or sensors; each bared end is flattened against a corresponding first ring crimped coaxially to the sheath alongside the relative hole, and sandwiched between this same ring and a second ring of electrically conductive and biocompatible material by which the sensor or electrode is fully encapsulated.

14 Claims, 2 Drawing Sheets

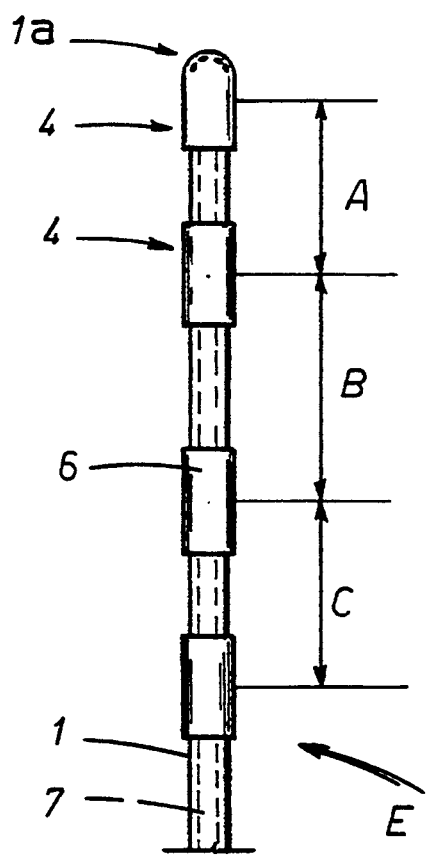
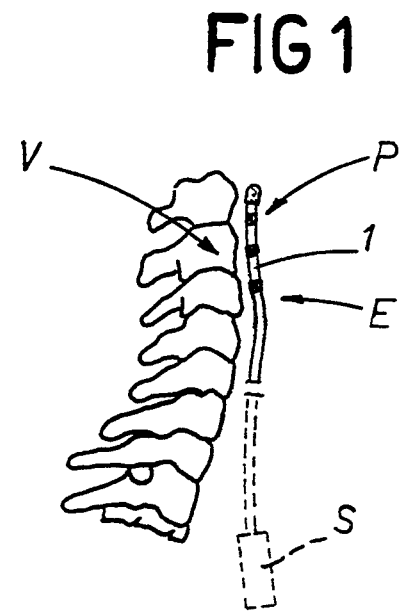
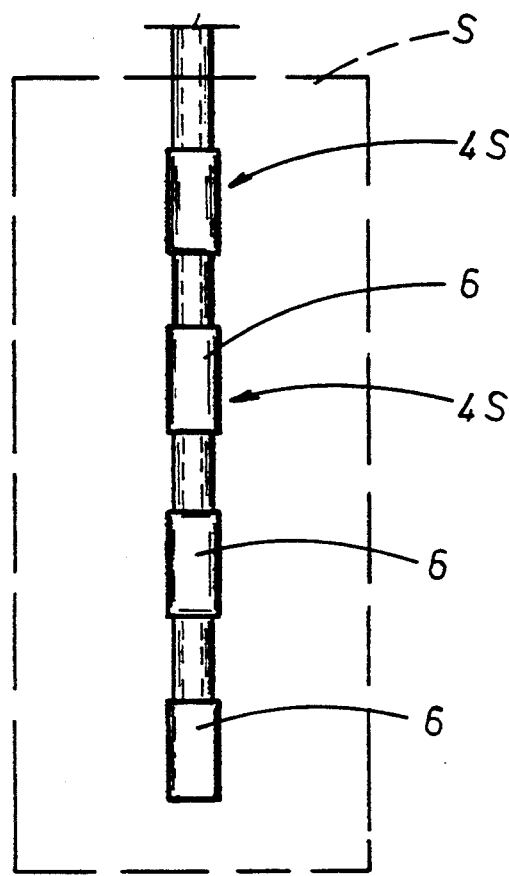
FIG 2
FIG 1

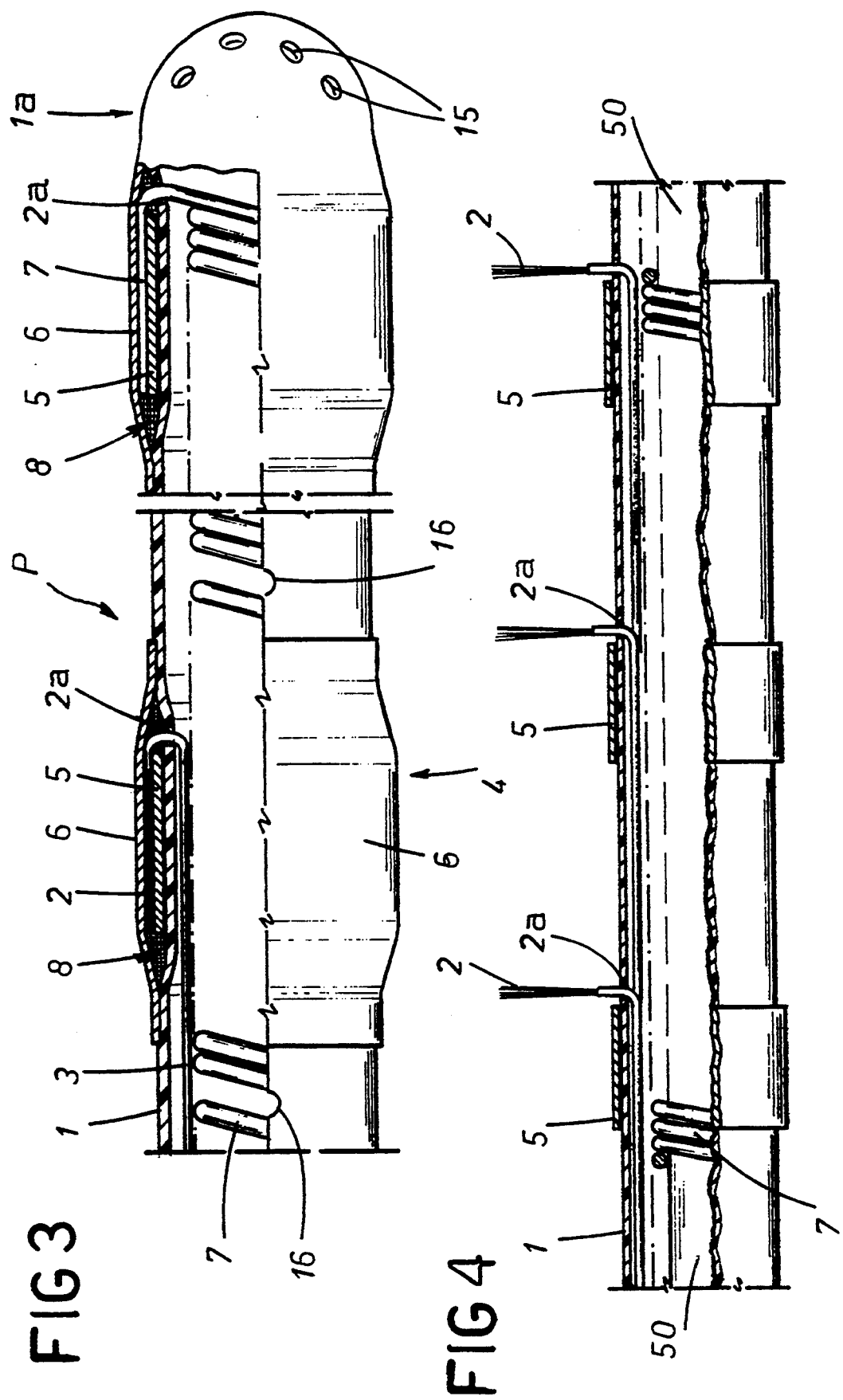

SPINAL ELECTRODE CATHETER

BACKGROUND OF THE INVENTION

The present invention relates to a spinal electrode catheter for stimulating areas of the vertebral column and the spinal bone marrow subcutaneously. It is being found currently in medical and surgical practice that optimum results are obtainable in the treatment of pathological conditions attributable to trauma of the vertebral column, affecting the spinal bone marrow in some instances, by inserting electrodes to stimulate the areas where functions (especially motor functions) have been impaired by such trauma.

Given however that this is a therapy of relatively recent origin, the prior art embraces no indwelling catheters designed specifically for implantation of the electrodes utilized to stimulate these areas (referred to in medicine as epidural); instead, the general practice is to adapt conventional cardiac pacemaker catheters for epidural implantation. Clearly enough, such adaptations are not entirely satisfactory, ensuring neither a swift and secure subcutaneous implant (which may also need to be permanent) nor even a wholly efficient treatment, at least when compared with the potential of the devices employed as cardiac pacemakers: in effect, the terminals or sensing elements of conventional cardiac pacemaker electrodes are disposed at fixed distances from each other and from the external stimulator; moreover, there are obvious differences in proportions, given the particular structure of the cardiac muscle (altogether different from the vertebral regions), and in the basic architecture adopted for the purposes of insertion, given that the anchorage and positioning requirements are not the same for a cardiac site as for vertebral sites, and will also vary in the latter instance according to the particular area traumatized.

This last-mentioned factor is of great importance for the patient, who has to undergo surgery of a delicate nature (e.g. laminectomy, or the removal of a lateral portion from the neural arch of one or more vertebrae) so that a vertebral anchorage can be effected; such operations generally do not tend to be secure and effective, either from the medical standpoint or that of the clarity of the signal at the poles of the electrodes afforded by the adapted catheter, and therefore can result in additional and not inconsiderable discomfort for the patient. In a dedicated solution aimed at solving problems of this nature, U.S. Pat. No. 4,379,462 discloses an electrode catheter comprising a tubular sheath designed to accommodate a plurality of electrically conductive wires establishing a corresponding plurality of electrodes; one end of each wire passes through the wall of the sheath to connect with a ring secured to the exterior of the sheath itself and providing the pole of the relative electrode, the remaining end being attached to the stimulator. The rings are spaced apart at an identical and selected distance one from another in such a way as to give an evenly distributed subcutaneous stimulation. The tubular sheath is also provided internally with a suitably rigid but flexible metal core designed to favor a subcutaneous insertion and to maintain the desired configuration of the catheter once in place.

Even this solution betrays drawbacks, however: the subcutaneous insertion cannot be effected without the aid of a guide element, preferably a stilet, which ensures that the catheter is correctly placed but must be removed following implantation, so that the duration of the operation is extended; neither does the metal core fully guarantee the performance of the tubular sheath, whether in respect of the rigidity required for insertion or of the degree of flexibility needed to adapt the electrode catheter to the cavity it will ultimately occupy. A further drawback stems from the fact that the sheath does not afford a faultless internal seal, especially at the breakout of the electrode wires, where the type of closure adopted tends not to give the mechanical and physiological guarantees appropriate to the purpose in question.

Accordingly, the object of the present invention is to overcome the drawbacks mentioned above through the provision of a spinal electrode catheter for use in subcutaneous stimulation of the vertebral column and spinal bone marrow, which can be swiftly and securely implanted in the patient and connected in such a way as to maintain a clean, uninterrupted electrical signal, and features a general structure tailored mechanically and biotechnologically to suit the specific field of therapy applied to the vertebral column.

SUMMARY OF THE INVENTION

The stated object is realized in a spinal electrode catheter according to the present invention, which comprises at least one first tubular outer sheath of biocompatible material, stopped at one end; the sheath is insertable into a subcutaneous vertebral cavity and accommodates a set of conductive wires, disposed substantially parallel one with another and insulated singly by respective second sheaths, each of which secured by one end to a relative terminal or sensor positioned externally of the first sheath in such a manner as to establish an electrode, and connected by the remaining end to a stimulator.

To advantage, the catheter disclosed comprises a flexible spiral wound element associated coaxially with and extending substantially the full length of the first sheath, thereby establishing an internal core from which the sheath derives rigidity to assist its insertion into the subcutaneous area, and a flexibility ensuring the adaptation of the inserted catheter to the cavity ultimately occupied following implantation, while functioning as a support for wires of which the ends associated with the sensors are bared from their insulating sheaths and caused to emerge from the first outer sheath by way of corresponding breakout holes; the catheter further comprises a first contact ring associated with each of the wires, positioned adjacent to the relative breakout hole and secured coaxially to the first sheath in such a way as to afford a support against which the bared end of the relative wire is bent and flattened, and a second encapsulating ring associated with each of the wires, fashioned from electrically conductive and biocompatible material and secured over the bared and flattened end of the wire and the first ring to complete the composition of the sensor or electrode.

BRIEF DESCRIPTION OF THE DRAWINGS

The invention will now be described in detail, by way of example, with the aid of the accompanying drawings, in which:

FIG. 1 is the schematic side elevation of a region of the vertebral column in which the electrode catheter according to the present invention might be implanted;

FIG. 2 is the side elevation of a spinal electrode catheter as in FIG. 1, illustrated in a quadrupolar embodiment and seen with certain parts omitted better to reveal others;

FIG. 3 is a further side elevation showing a part of the electrode catheter, seen enlarged and with certain parts illustrated in section;

FIG. 4 is a side elevation showing another part of the electrode catheter, enlarged and with certain parts in section, and illustrating an intermediate stage in the assembly of the sensors or electrodes.

DESCRIPTION OF THE PREFERRED EMBODIMENTS

With reference to the accompanying drawings, an electrode catheter for subcutaneous stimulation of selected areas of the vertebral column, denoted V in FIG. 1, and of the spinal bone marrow, consists essentially in a first outer sheath 1 fashioned from biocompatible material (e.g. polyurethane), which is tubular, stopped at one extremity 1a and insertable subcutaneously into the selected area of the column.

The tubular outer sheath 1 accommodates a set of electrically conductive wires 2 (see FIGS. 2 and 4) disposed mutually parallel and insulated singly by respective second sheaths 3; each such wire 2 is connected at one end to a corresponding sensor or terminal 4 located externally of the first outer sheath 1, thereby establishing an electrode P, and at the remaining end to the respective contact 4S of a conventional external stimulator S illustrated by phantom lines in FIGS. 1 and 2.

In addition to the components mentioned thus far, the electrode catheter comprises a flexible spiral wound element 7, a set of first contact rings 5 and a corresponding set of second encapsulating rings 6 (see FIGS. 3 and 4).

More exactly, the flexible spiral wound element 7 is positioned internally of and coaxially with the outer sheath 1, extending substantially the entire length of the sheath in such a way as to establish a core by which the resulting structure is invested both with rigidity, when implanted in the selected subcutaneous region, and with flexibility enabling its adaptation to the cavity ultimately occupied.

The flexible element 7 is in effect an electrically conductive spiral wound wire rigidly connected to the stopped end of the outer sheath 1 and serving also as a means of supporting the wires 2, of which the ends are bared a suitable length from their respective second sheaths 3 and emerge to connect with the relative sensors 4 by way of corresponding breakout holes 2a formed in the sheath 1.

The width or internal diameter of the spiral wound element 7 is also such as to allow the passage of a coaxial mandrel or stilet 50 (shown schematically in FIG. 4) that serves to increase the rigidity of the catheter, hence the facility with which it is inserted to accomplish implantation, and is easily withdrawn thereafter.

Each of the single breakout holes 2a occupied by an emerging wire 2 is flanked by a corresponding first ring 5 crimped coaxially onto the outer sheath 1 in such a way as to provide an electrically conductive contact element against which to flatten the bared end of the relative wire 2; the ring 5 is located preferably on the proximal side of the respective hole 2a, relative to the distal stopped end of the outer sheath 1, in such a way that the bared end of the wire can be anchored to best possible effect.

The second ring 6, also electrically conductive, is fashioned in biocompatible material and positioned stably over the end of the wire 2 flattened against the first ring 5 in such a manner as to encapsulate both of these components and complete the assembly of the sensor 4 or electrode P.

8 denotes biocompatible sealing means by which to ensure a tight encapsulation of each electrode p assembled in the mannner described above i.e. the second ring 6, wire 2, first ring 5 and sheath 1; such means 8 consist in a biocompatible medical adhesive in which the entire area of the breakout, hence of the electrode or terminal, is embedded. As clearly discernible from FIGS. 2 and 3, second rings 6 are fitted to the distal end 1a of the tubular sheath 1, and preferably to the remaining end also, thereby performing the dual function of electrode P and contact 4S for the stimulator S, and a capping element for the catheter as a whole.

More exactly, the distal end 1a is capped by a second ring 6 fashioned with a domed head, inserted into and rigidly associated with the relative end of the flexible spiral wound element 7; thus, being electrically conductive, the spiral wound element 7 can function additionally as a conductor (instead of a wire 2).

Likewise from FIG. 2, it will be observed in the case of a quadrupole catheter that the distances A; B and C between centers of the electrodes P are dissimilar, in order to optimize the stimulation; in the example illustrated, in effect, the distance denoted A (separating the centers of the distal and penultimate electrodes) is equal to the distance denoted C (between the proximal and antepenultimate electrodes) though these same distances A and C are dissimilar to the distance B separating the centers of the two intermediate electrodes. Not least among the advantages of this particular solution is that the electrode catheter can be used for stimulation purposes or for monitoring signals, as required, by pairing the electrodes differently.

An additional expedient afforded by the electrode catheter disclosed, deriving directly from the particular features of its construction, is that the second ring 6 capping the distal end 1a can be pierced with holes 15 so as to permit of infusing drugs into the region occupied by the catheter, using the spiral wound element 7 as a feed tube; similarly, an increased capacity can be achieved by positioning further lateral holes 16 in the surface of the sheath 1 to coincide with gaps in the spiral wound element 7, thereby improving the flow and distribution of any such infusion.

The process of assembling an electrode according to the invention comprises the steps of:

inserting the wires 2 (in number commensurate with the type of catheter selected) into the tubular outer sheath 1, in such a way that each bared end is positioned adjacent to a respective hole 2a;

coaxially inserting the spiral wound element 7 into and through the entire length of the sheath 1 and if appropriate, exploiting the free end as the electrical connection to the distal electrode P;

positioning and crimping the first rings 5 onto the external surface of the outer sheath at points adjacent to the bared ends of the wires 2, then bending and flattening at least the bared end of each wire forcibly against the ring 5 (see FIG. 4), with the assistance of the backing afforded by the spiral wound element 7;

passing and positioning the second rings 6 over the tubular outer sheath 1 and into alignment with the first rings, for example by rolling, in such a manner that the bared end of each wire 2 remains sandwiched between the two relative rings and 6. Thereafter, the medical adhesive aforementioned is spread over each of the electrode assemblies thus composed.

In practice, a spinal electrode catheter embodied in the manner described above can be inserted with considerable speed into the vertebral region of a patient without any special auxiliary guide means, inasmuch as the core provided by the spiral wound element affords sufficient rigidity (in conjunction with a mandrel or stilet) to ensure that there will be no difficulty experienced in penetration of any subcutaneous vertebral site, while at the same time yielding flexibly (following removal of the stilet) to allow adaptation of the catheter to the cavity ultimately occupied; also, the electrode associated with the distal end 1a of the sheath 1 functions to advantage as a probe.

The electrodes illustrated also feature a compact type of structure, and are designed with vertebral stimulation specifically in mind, besides affording the clear advantage that their number can be varied according to the nature of the treatment envisaged; for example, the electrode catheter can be bipolar or quadrupolar according to the size of the region to be treated, and without prejudice in any sense to the features already described above. Moreover, the structure of the electrodes ensures a reliable, clean signal thanks to the manner of anchoring the wire 2, i.e. sandwiched between the rings 5 and 6.

What is claimed:

1. A spinal electrode catheter for the subcutaneoas stimulation of areas of the vertebral column and the spinal bone marrow, comprising at least one first tubular outer sheath fashioned in biocompatible material, stopped at one end and insertable into a subcutaneous vertebral area and accommodating a set of electrically conductive wires disposed substantially parallel one with another and insulated individually by respective second sheaths, each of which connected by one end to a corresponding terminal or sensor positioned externally of the first sheath in such a way as to establish an electrode, and by the remaining end to a stimulator, and further comprising:
    a flexible spiral wound element associated co-axially with and extending substantially the full length of the first sheath in such a way as to establish an internal core by which the sheath is invested with rigidity during insertion into the subcutaneous area and with flexibility allowing adaptation of the electrode catheter to the cavity ultimately occupied following implantation, while functioning as a support for said wires of which the ends associated with the sensors are bared from their insulating sheaths and caused to emerge from the first outer sheath by way of corresponding breakout holes;
    a first contact ring associated with each of the wires, positioned adjacent to the relative breakout hole and secured coaxially to the first sheath in such a manner as to afford a support against which the bared end of the wire is bent and flattened;
    a second encapsulating ring associated with each wire, fashioned from electrically conductive and biocompatible material and secured over the bared and flattened end of the wire and the first ring in such a way as to complete the composition of the sensor or electrode.

2. An electrode catheter as in claim 1, wherein each electrode assembly also comprises biocompatible sealing means positioned to coincide with the second encapsulating rings and consisting of a biocompatible medical adhesive, in which the second ring, the bared end of the relative wire, the first ring and the corresponding part of the first sheath are permanently embedded.

3. An electrode catheter as in claim 1, wherein the flexible element consists of a spiral wound metal wire connected to the stopped end of the first outer sheath.

4. An electrode catheter as in claim 1, wherein each of the first contact rings is positioned or the proximal side of the emerging wire in relation to the distal stopped end of the first outer sheath.

5. An electrode catheter as in claim 1, wherein the sensor or second ring nearest the stopped end of the first outer sheath is connected electrically to the end of said flexible spiral wound element, said element consisting of an electrically conductive material and of internal diameter or width such as to allow the passage of a coaxial mandrel or stylet.

6. An electrode catheter as in claim 1, wherein the distances between centers of adjacent sensors or electrodes are dissimilar one from another.

7. An electrode catheter as in claim 5, wherein at least the sensor or electrode nearest the stopped end of the first outer sheath is pierced with a plurality of holes serving to allow an infusion of drugs conveyed by way of the catheter.

8. An electrode catheter as in claim 1, wherein the tubular outer sheath affords a plurality of holes distributed uniformly along its length, serving to allow an infusion of drugs conveyed by way of the catheter.

9. A method of assembling an electrode catheter as in claim 1, comprising the steps of:
    inserting the wires into the tubular outer sheath in such a way that each bared end is positioned adjacent to a respective hole;
    coaxially inserting the spiral wound element into and through substantially the entire length of the sheath;
    positioning and securing the first contact rings at points adjacent to the bared ends of the wires, then bending and flattening at least the bared end of each wire against the relative ring;
    positioning and securing the second rings over the first rings such that the bared end of each wire remains sandwiched between the relative rings.

10. A method of assembling an electrode catheter as in claim 9, comprising the further step, implemented concurrently with that of positioning and securing the second rings, of applying sealing means to each of the assemblies comprising a second ring, the bared end of a wire and a first contact ring.

11. A method of assembling an electrode catheter as in claim 2 comprising the steps of:
    inserting the wires into the tubular outer sheath in such a way that each bared end is positioned adjacent to a respective hole;
    coaxially inserting the spiral wound element into and through substantially the entire length of the sheath;
    positioning and securing the first contact rings at points adjacent to the bared ends of the wires, then bending and flattening at least the bared end of each wire against the relative ring;

positioning and securing the second rings over the first rings such that the bared end of each wire remains sandwiched between the relative rings.

12. A method of assembling an electrode catheter as in claim 3 comprising the steps of:
   inserting the wires into the tubular outer sheath in such a way that each bared end is positioned adjacent to a respective hole;
   coaxially inserting the spiral wound element into and through substantially the entire length of the sheath;
   positioning and securing the first contact rings at points adjacent to the bared ends of the wires, then bending and flattening at least the bared end of each wire against the relative ring;
   positioning and securing the second rings over the first rings such that the bared end of each wire remains sandwiched between the relative rings.

13. A method of assembling an electrode catheter as in claim 4 comprising the steps of:
   inserting the wires into the tubular outer sheath in such a way that each bared end is positioned adjacent to a respective hole;
   coaxially inserting the spiral wound element into and through substantially the entire length of the sheath;
   positioning and securing the first contact rings at points adjacent to the bared ends of the wires, then bending and flattening at least the bared end of each wire against the relative ring;
   positioning and securing the second rings over the first rings such that the bared end of each wire remains sandwiched between the relative rings.

14. A method of assembling an electrode catheter as in claim 5 comprising the steps of:
   inserting the wires into the tubular outer sheath in such a way that each bared end is positioned adjacent to a respective hole;
   coaxially inserting the spiral wound element into and through substantially the entire length of the sheath;
   positioning and securing the first contact rings at points adjacent to the bared ends of the wires, then bending and flattening at least the bared end of each wire against the relative ring;
   positioning and securing the second rings over the first rings such that the bared end of each wire remains sandwiched between the relative rings.

* * * * *